US00PP26666P2

(12) United States Plant Patent
Smith

(10) Patent No.: US PP26,666 P2
(45) Date of Patent: Apr. 26, 2016

(54) DENDRANTHEMA PLANT NAMED 'FIREWORKS IGLOO'

(50) Latin Name: *Chrysanthemum×morifolium*
Varietal Denomination: Fireworks Igloo

(71) Applicant: Mark A. Smith, Fort Myers, FL (US)

(72) Inventor: Mark A. Smith, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 140 days.

(21) Appl. No.: 13/998,710

(22) Filed: Nov. 26, 2013

(51) Int. Cl.
*A01H 5/02* (2006.01)

(52) U.S. Cl.
USPC ..... Plt./287

(58) Field of Classification Search
USPC ..... Plt./287
See application file for complete search history.

*Primary Examiner* — Keith Robinson
(74) *Attorney, Agent, or Firm* — C. A. Whealy

(57) ABSTRACT

A new and distinct cultivar of Dendranthema plant named 'Fireworks Igloo', characterized by its upright, outwardly spreading and uniformly mounded plant habit; freely branching habit; dense and full plant form; uniform and freely flowering habit; decorative-type inflorescences; lavender-colored ray florets; and good garden performance and winter hardiness.

1 Drawing Sheet

Botanical designation: *Chrysanthemum×morifolium.*
Cultivar denomination: 'FIREWORKS IGLOO'.

BACKGROUND OF THE INVENTION

The present invention relates to a new and distinct Dendranthema plant, botanically known as *Chrysanthemum×morifolium*, commercially grown as a perennial garden-type Dendranthema plant, and hereinafter referred to by the cultivar name 'Fireworks Igloo'.

The objective of the breeding program is to create new perennial garden-type Dendranthema plants having uniformly mounding plant habit, inflorescences with desirable inflorescence forms, attractive floret colors and good winter hardiness and garden performance.

The new Dendranthema plant originated from a cross-pollination made by the Inventor in September, 2007, in Bogota, Colombia of a proprietary selection of *Chrysanthemum×morifolium* identified as code number H7486, not patented, as the female, or seed, parent with a proprietary selection of *Chrysanthemum×morifolium* identified as code number H7527, not patented, as the male, or pollen, parent. The new Dendranthema plant was discovered and selected by the Inventor as a single flowering plant within the progeny of the stated cross-pollination in a controlled greenhouse environment in Alva, Fla. on Oct. 30, 2008.

Asexual reproduction of the new Dendranthema plant by vegetative cuttings was first conducted in a controlled greenhouse environment in Alva, Fla. in January, 2008 and such asexual propagation has shown that the unique features of this new Dendranthema plant are stable and reproduced true to type in successive generations.

SUMMARY OF THE INVENTION

Plants of the new Dendranthema have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fireworks Igloo'. These characteristics in combination distinguish 'Fireworks Igloo' as a new and distinct garden-type Dendranthema plant:

1. Upright, outwardly spreading and uniformly mounded plant habit.
2. Freely branching habit; dense and full plant form.
3. Uniform and freely flowering habit.
4. Decorative-type inflorescences with quilled-shaped ray florets.
5. Lavender-colored ray florets.
6. Natural season flowering occurs about September 23 in the Northern Hemisphere.
7. Good garden performance and winter hardiness.

In side-by-side comparisons, plants of the new Dendranthema differ from plants of the female parent selection in the following characteristics:

1. Plants of the new Dendranthema are larger than plants of the female parent selection.
2. Plants of the new Dendranthema flower about one week later than plants of the female parent selection when grown under natural season conditions.
3. Plants of the new Dendranthema have larger inflorescences than plants of the female parent selection.
4. Plants of the new Dendranthema and the female parent selection differ in ray floret shape and color as plants of the female parent selection have light lavender-colored ligulate-shaped ray florets.

In side-by-side comparisons, plants of the new Dendranthema differ from plants of the male parent selection in the following characteristics:

1. Plants of the new Dendranthema are rounded than and not as upright as plants of the male parent selection.

2. Plants of the new Dendranthema and the male parent selection differ in ray floret color as plants of the male parent selection have coral red-colored ray florets.

Plants of the new Dendranthema can be compared to plants of *Chrysanthemum×morifolium* 'Yovictoria', disclosed in U.S. Plant Pat. No. 13,799. In side-by-side comparisons, plants of the new Dendranthema differ from plants of 'Yovictoria' in the following characteristics:

1. Plants of the new Dendranthema are more compact than plants of 'Yovictoria'.
2. Plants of the new Dendranthema have larger inflorescences than plants of 'Yovictoria'.
3. Plants of the new Dendranthema and 'Yovictoria' differ in ray floret shape as plants of 'Yovictoria' have elongated oblong-shaped ray florets.

BRIEF DESCRIPTION OF THE PHOTOGRAPHS

The accompanying photographs illustrate the overall appearance of the new Dendranthema showing the colors as true as it is reasonably possible to obtain in colored reproductions of this type. Colors in the photographs may differ slightly from the color values cited in the detailed botanical description which accurately describe the colors of the new Dendranthema plant.

The photograph at the bottom of the sheet comprises a side perspective view of a typical flowering plant of 'Fireworks Igloo' grown in a container.

The photograph at the top of the sheet is a close-up view of typical inflorescences of 'Fireworks Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type Dendranthema production. During the production of the plants, day temperatures averaged 27.8° C. and night temperatures averaged 15.6° C. Plants were 19 weeks old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Fireworks Igloo'.

Parentage:

*Female, or seed, parent*.—Proprietary selection of *Chrysanthemum×morifolium* identified as code number H7486, not patented.

*Male, or pollen, parent*.—Proprietary selection of *Chrysanthemum×morifolium* identified as code number H7527, not patented.

Propagation:

*Type*.—Terminal vegetative cuttings.

*Time to initiate roots*.—About four days at temperatures about 21° C.

*Time to produce a rooted young plant*.—About ten to twelve days at temperatures about 21° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching, dense.

Plant description:

*Plant and growth habit*.—Perennial garden-type Dendranthema plant with decorative-type inflorescences; upright, outwardly spreading and uniformly mounding plant habit; strong and vigorous growth habit.

*Branching habit*.—Freely branching habit, about seven primary lateral branches each with multiple secondary and tertiary branches; dense and full plant form; pinching is not required.

*Plant height*.—About 26 cm.

*Plant width*.—About 46 cm.

*Lateral branches*.—Length: About 23 cm. Diameter: About 4 mm. Internode length: About 1.6 cm. Strength: Strong. Texture: Pubescent; longitudinally ridged. Color: Close to 146B.

*Leaves*.—Arrangement: Alternate, simple. Length: About 3.3 cm. Width: About 2.3 cm. Apex: Acute. Base: Attenuate. Margin: Palmately lobed, sinuses between lateral lobes mostly parallel and medium. Texture, upper and lower surfaces: Pubescence; veins prominent on lower surface. Luster, upper and lower surfaces: Matte. Venation pattern: Pinnate. Color: Developing leaves, upper surface: Close to N137A. Developing leaves, lower surface: Close to N137D. Fully expanded leaves, upper surface: Close to 146A; venation, close to 147B to 147C. Fully expanded leaves, lower surface: Close to 147B; venation, close to 147C. Leaf petioles: Length: About 1 cm. Diameter: About 2 mm. Aspect: Somewhat upright. Texture, upper and lower surfaces: Pubescent. Color, upper and lower surfaces: Close to 147C.

Inflorescence description:

*Type and arrangement*.—Decorative-type inflorescence form with quilled-shaped ray florets; disc and ray florets arranged acropetally on a capitulum; inflorescences face mostly upright and held above the foliar plane on strong peduncles.

*Fragrance*.—Faintly fragrant, sour.

*Flowering response*.—Under natural season conditions, plants flower about September 23 in the Northern Hemisphere.

*Postproduction longevity*.—Inflorescences maintain good color and substance for about six weeks on the plant; inflorescences persistent.

*Quantity of inflorescences*.—Freely flowering habit with about 88 inflorescences developing per lateral branch.

*Inflorescence buds*.—Height: About 1 cm. Diameter: About 1.1 cm. Shape: Oblate, flat-topped. Color: Close to 84C.

*Inflorescence size*.—Diameter: About 3 cm. Depth (height): About 1.7 cm. Disc diameter: About 3 mm; inconspicuous. Receptacle diameter: About 1.2 cm. Receptacle height: About 5 mm. Receptacle color: Close to 147B to 147C.

*Ray florets*.—Quantity and arrangement: About 180 ray florets develop per inflorescence and arranged in about twelve whorls. Length: About 1.5 cm; length of fused portion, about 1.4 cm. Diameter: About 1 mm. Shape: Quilled, slender tubular with spoon-shaped apex. Apex: Emarginate. Margin: Free part, entire. Orientation: Initially upright, then about 75° from vertical. Texture, upper and lower surfaces: Smooth, glabrous; velvety; longitudinally ribbed. Color: When opening, upper surface: Close to 84C. When opening, lower surface: Close to 76A. Fully opened, upper surface: Close to 84B; color becoming closer to 84C with development. Fully opened, lower surface: Close to 76B to 76C; color becoming closer to 76C with development.

*Disc florets*.—Quantity and arrangement: About 28 fused disc florets develop per inflorescence and massed at the center of the capitulum; disc florets are only visible when inflorescences are fully developed. Length: About 5 mm. Diameter: Less than 1 mm. Shape: Tubular, elongated. Apex: Five-pointed. Texture, inner and outer surfaces: Smooth, glabrous. Color, immature: Apex: Close to 7A. Mid-section and base: Close to 145D. Color, mature: Apex: Close to 8B. Mid-section and base: Close to 145D.

*Phyllaries*.—Quantity and arrangement: About 30 phyllaries develop per inflorescence and arranged in about 2.5 whorls. Length: About 5 mm. Width: About 2.5 mm. Shape: Elliptical. Apex: Acute. Base: Truncate. Margin: Entire; membraneous. Texture, upper surface: Smooth, glabrous. Texture, lower surface: Pubescent. Color, upper and lower surfaces: Close to 147B.

*Peduncles*.—Length, terminal peduncle: About 5.2 cm. Length, fourth peduncle: About 5.5 cm. Diameter, terminal peduncle: About 1.5 mm. Angle: Mostly upright or curving upright. Strength: Strong. Texture: Pubescent. Color: Close to 148B.

*Reproductive organs*.—Androecium (present on disc florets only): Stamen number: Five per floret. Filament length: About 2 mm. Filament color: Close to 145D. Anther length: About 1.5 mm. Anther shape: Narrowly oblong. Anther color: Close to 15A. Pollen amount: Scarce. Pollen color: Close to 15A. Gynoecium (present on ray and disc florets): Pistil length: About 5 mm. Stigma shape: Bi-parted. Stigma color: Close to 13B. Style length: About 2 mm. Style color: Close to 145D. Ovary color: Close to NN155D.

*Seeds and fruits*.—Seed and fruit production has not been observed on plants of the new Dendranthema.

Disease & pest resistance: Resistance to pathogens and pests common to Dendranthema plants has not been observed on plants grown under commercial production conditions.

Garden performance & temperature tolerance: Plants of the new Dendranthema have demonstrated excellent garden performance, are hardy to USDA Zone 5 and tolerate high temperatures of about 37.8° C.

It is claimed:

1. A new and distinct Dendranthema plant named 'Fireworks Igloo' as illustrated and described.

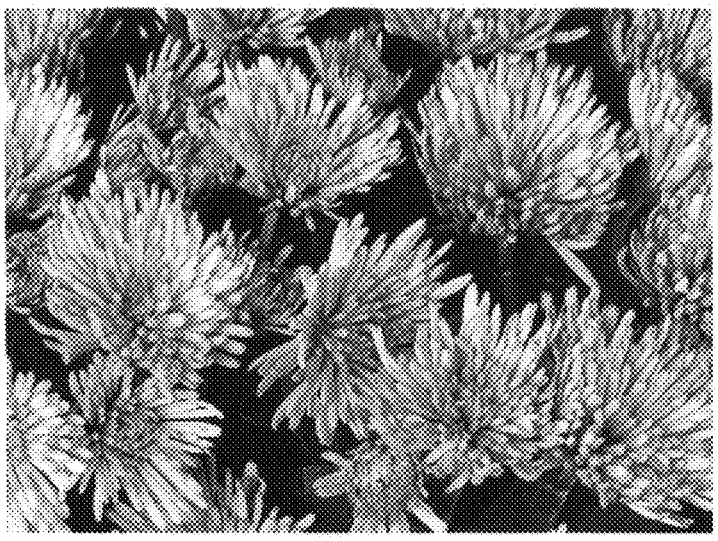
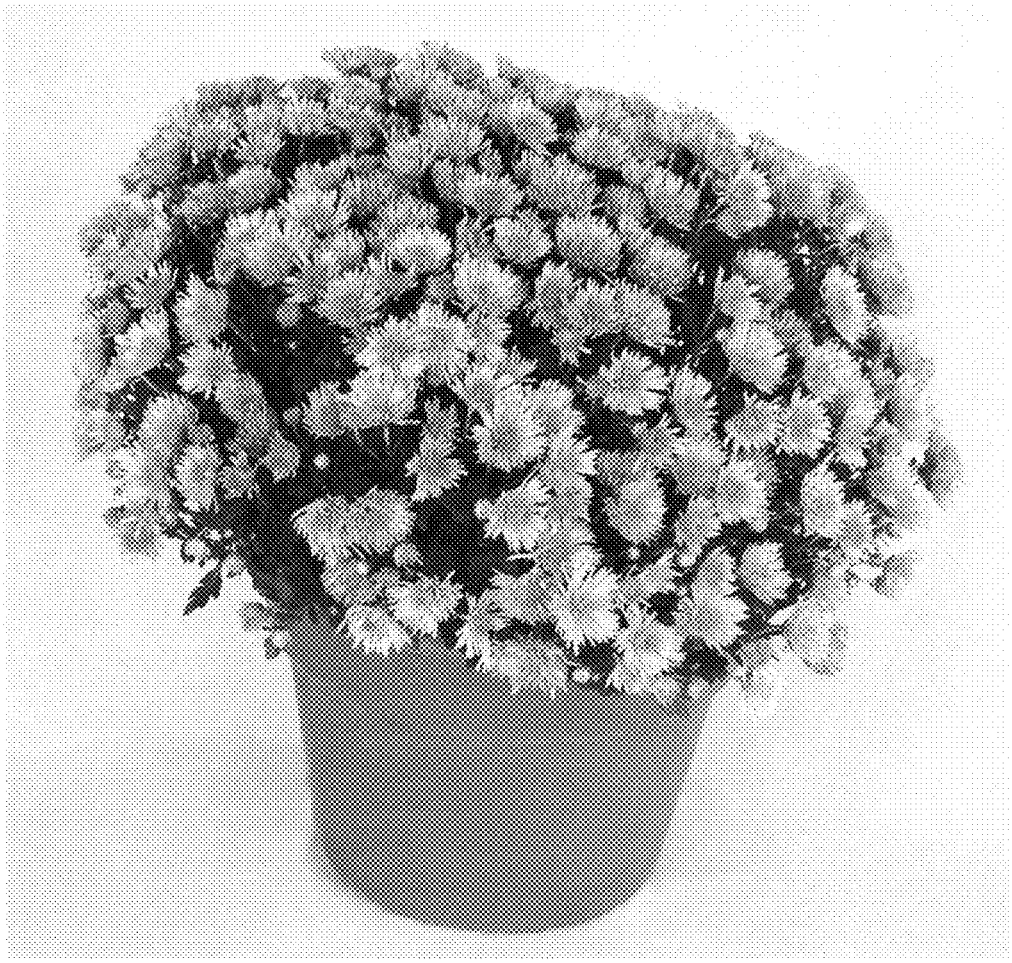

* * * * *